Figure 1:
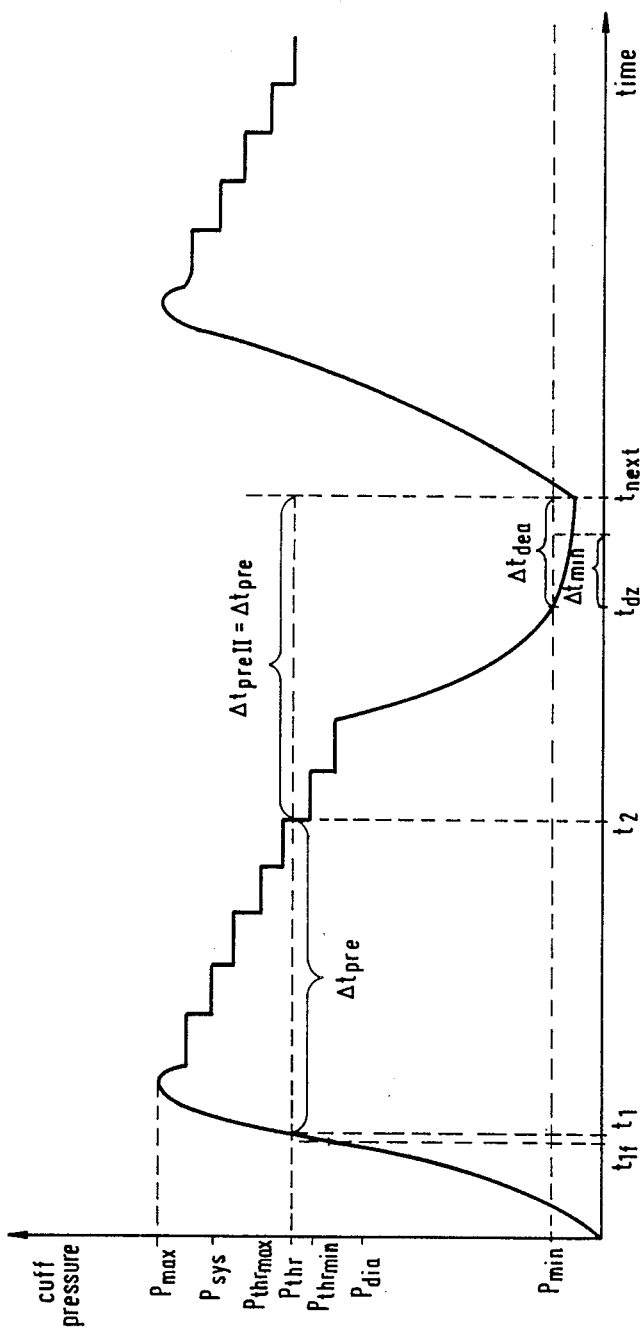

United States Patent [19]

Frankenreiter

[11] Patent Number: 4,967,757

[45] Date of Patent: Nov. 6, 1990

[54] METHOD FOR MEASURING BLOOD PRESSURE AND APPARATUS FOR AUTOMATED BLOOD PRESSURE MEASURING

[75] Inventor: Michael Frankenreiter, Sindelfingen, Fed. Rep. of Germany

[73] Assignee: Hewlett-Packard Company, Palo Alto, Calif.

[21] Appl. No.: 339,786

[22] Filed: Apr. 18, 1989

[30] Foreign Application Priority Data

Aug. 1, 1988 [EP] European Pat. Off. ........ 88112449.9

[51] Int. Cl.$^5$ .............................................. A61B 5/02
[52] U.S. Cl. .................................................. 128/682
[58] Field of Search ........................ 128/672, 677–686

[56] References Cited

U.S. PATENT DOCUMENTS

| | | | |
|---|---|---|---|
| 4,543,962 | 10/1985 | Medero et al. | 128/680 X |
| 4,546,775 | 10/1985 | Medero | 128/681 |
| 4,625,277 | 11/1986 | Pearce et al. | 128/681 X |
| 4,754,761 | 7/1988 | Ramsey, III et al. | 128/683 |
| 4,796,184 | 1/1989 | Bahr et al. | 128/681 X |

Primary Examiner—William E. Kamm

[57] ABSTRACT

A method of non-invasive blood pressure measuring is conducted in the so-called stat mode, wherein several subsequent measurement cycles occur. A next subsequent blood pressure measuring cycle starts at a time that is a function of a cycle specific time interval length of a preceding measuring cycle. An apparatus comprising a time delay module for retarding start of a next cycle, a time increment register for storing a cycle specific time interval length of a preceding measuring cycle. The time delay module allows start of a next subsequent cycle as a function of the time interval length of the preceding cycle.

11 Claims, 4 Drawing Sheets

METHOD FOR MEASURING BLOOD PRESSURE AND APPARATUS FOR AUTOMATED BLOOD PRESSURE MEASURING

DESCRIPTION

The present invention relates to a method for measuring blood pressure, comprising the steps of applying a blood pressure cuff about a subject's limb containing an artery; inflating said cuff to a pressure $p_{max}$ above the systolic pressure $p_{sys}$, thereby occluding said artery, reducing cuff pressure from $p_{max}$ to a pressure $p_{min}$ below the diastolic pressure $p_{dia}$, thereby permitting an increasing flow through the progressively less occluded artery, detecting of effects at the cuff caused by said increasing flow through that progressively less occluded artery, processing said detected effects in processing means and displaying said processed effects as subject's actual blood pressure values, and conducting a next subsequent blood pressure measuring cycle after the end of a dead time interval $\Delta t_{dea}$, said dead time interval starting at a time $t_{dz}$, after cuff pressure reaching $p_{min}$.

The invention further relates to an apparatus for automated blood pressure measuring, in particular for cyclic measuring of blood pressure, the apparatus comprising an inflatable and deflatable pressure cuff, said cuff being applicable about a subject's limb containing an artery, means for inflating said cuff to a pressure $p_{max}$ above the systolic pressure $p_{sys}$, thereby occluding said artery, means for reducing cuff pressure from $p_{max}$ to a pressure $p_{min}$ below the diastolic pressure $p_{dia}$, thereby permitting an increasing flow through the progressively less occluded artery, means for detecting of effects at the cuff caused by said increasing flow through the progressively less occluded artery, processing means for processing said detected effects and for displaying said processed effects as subject's actual blood pressure values, said processing means further comprising means for retarding the start of a next subsequent measuring cycle until a dead time interval $\Delta t_{dea}$ has ended.

Such so-called "non-invasive" blood pressure measuring methods and apparatus are well-known in the art and known as sphygmomanometers. A similar method and a similar apparatus is known from EP-A No. 2- 0 207 807.

During such non-invasive sphygmomanometric measurements, an inflatable cuff is suitably located around a limb of a subject, for example a human, and is inflated up to a predetermined pressure $p_{max}$ above the systolic pressure $p_{sys}$, thereby occluding an artery. The limb may be an arm, in particular the upper arm, a foot, or a finer of subject. Thereupon, cuff pressure is reduced, thereby permitting an increasing flow through the progressively less occluded artery. The effects at the cuff may be detected by the auscultative method, thereby detecting the so-called "Korotkoff noise" caused by the artery during deflating of cuff.

A further well-known method is the so-called "oscillometric method", for example as described within EP-A No. 2-0 208 520.

The oscillometric method of measuring blood pressure is one of the most popular methods in commercially available systems. This method relies on measuring changes in arterial counterpressure, such as imposed by the inflatable cuff which is controllably relaxed or inflated. The cuff pressure is reduced in predetermined increments, and at each pressure level fluctuations are monitored. The resulting signals typically consist of the DC voltage with small superimposed variational component caused by arterial blood pressure pulsations. After suitable filtering to reject the DC component and to provide amplification, peak pulse amplitudes above a given base line are measured and stored. As deflating of the cuff continues, the peak amplitudes will normally increase from a lower level to a relative maximum, and thereafter will decrease. The lowest cuff pressure at which the oscillation has a maximum value is representative of mean arterial pressure. Systolic and diastolic pressures can be derived as a predetermined fraction of mean arterial pressure, or by more sophisticated methods of direct processing of the oscillatory complexes.

In some applications, several subsequent measurement cycles are necessary and have become an essential aspect of human and veterinary treatment. Such subsequent measurements are preferably conducted in emergency rooms, intensive and critical care units, and in the operating theatre.

One problem on conducting subsequent measurement cycles is the dimension of the pause or death-time between two subsequent cycles. Dead time is understood as an interval starting from a time at which the deflated cuff has reached a minimum pressure, for example 6.66 kPa (5 mmHg), at which minimum pressure the cuff is deflated approximately totally and ending at the start time $t_{next}$ of the next subsequent cycle.

The known methods and the known apparatus for conducting said measurements in a cyclic manner, so-called "stat-mode", use a constant predetermined dead time interval.

If the dead time interval is chosen long, this may be more agreeable to the patient. Long dead time intervals, however, do not allow a lot of measurement cycles within a predetermined time interval. For example, the effects of a drug, applicated to the patient during a surgical operation need to be supervised by blood measurement cycles with 20 or 30 second lengths.

If a very short dead time interval is used, it may be very disagreeable for the patient. Furthermore, if a overall time of a measurement cycle is very long, for example based on artifacts during measurement caused by movements of the patient, a short dead time interval is not convenient because of possible blood backwash reflecting to the heart of the patient. Time-consuming measurement cycles are necessary, if patient's systole and diastole are far apart.

Nevertheless, all known methods and apparatus for automated non-invasive blood pressure measurements use constantly preselected dead time intervals between two subsequent measurement cycles.

It is, therefore, an object of the present invention to provide a method and an apparatus for measuring blood pressure as initially indicated using dead time intervals being convenient to the individual subject to be measured.

This object is achieved by a method, comprising the step of starting a next subsequent blood pressure measuring cycle at a time $t_{next}$ that is a function of a cycle specific time interval $\Delta t_{pre}$ of the preceding measuring cycle. This object is further achieved by an apparatus with means for retarding start of the next cycle, said means comprising time-incrementing means for storing a cycle specific time interval $\Delta t_{pre}$ of a preceding measuring cycle, said retarding means allowing a start of a next subsequent cycle as a function of said time interval $\Delta t_{pre}$.

According to the invention, each dead time interval is adapted to the individual subject to be measured and is adapted to the preceding measuring cycle during a cyclic measurement, in particular in stat-mode measurements.

The cycle specific time interval $\Delta t_{pre}$ may be the overall time for conducting said preceding measuring cycle. In particular, the dead time interval may be a fraction of the overall time interval. As a result, a short time interval $\Delta t_{pre}$ leads to a short dead time interval, and on the contrary, a long time interval $\Delta t_{pre}$ leads to a long dead dead time interval. Further, if the cycle specific time interval $\Delta t_{pre}$ varies during several measurement cycles, for example in response to drugs applied to patient, the dead time interval is automatically adapted cycle by cycle to the varying preceding measuring cycle. The apparatus according to the invention automatically stores time increments of a preceding cycle and allows a start of a next subsequent cycle after a dead time interval that is a function of said time increments.

So, according to the invention, both a dead time interval adaption to the individual subject and an automatic adaption to varying measurement cycle intervals is achieved. As a result, blood pressure measuring is more agreeable to the subject.

According to another aspect of the invention, the time interval $t_{pre}$ starts at a time $t_1$ after reaching a threshold cuff pressure $p_{thr}$ during inflating of the cuff, and ends at a time $t_2$ after reaching the said threshold pressure $p_{thr}$ again during the cuff pressure reducing step of said cycle.

This has the advantage that the time interval $\Delta t_{pre}$ depends on the varying cuff pressures during measuring cycle, where said varying cuff pressures are essential factors on which the measuring cycle time depends. The time interval $t_{pre}$ corresponds to a time during which the cuff pressure being above a threshold cuff pressure. The dead time interval may be, for example, elected as identical with the time interval $\Delta t_{pre}$.

According to another aspect of the invention, the said threshold pressure $\Delta t_{pre}$ corresponds to the mean blood pressure $p_{mea}$ of the subject to be measured.

This has the advantage that the threshold pressure is adapted to a particular blood pressure value representing to the actual condition of the subject to be measured. As a result, a subsequent next cycle depends on both an absolute time interval of the preceding cycle and the blood pressure measured during said preceding cycle.

According to another aspect of the invention, the threshold cuff pressure $p_{thr}$ varies within the range.

$$p_{thrmin} \leq p_{thr} \leq p_{thrmax}.$$

This has the advantage, that, in particular if the threshold cuff pressure $p_{thr}$ corresponds to the mean pressure $p_{mea}$ of the subject to be measured, $p_{thr}$ cannot exceed minimum and maximum limits. This assures that if an extreme shift of the mean blood pressure $p_{mea}$ occurs, the corresponding dead time interval neither becomes too short nor unnecessarily long.

According to another aspect of the invention, for measuring the blood pressure of human, the threshold cuff pressure $p_{thr}$ is limited to the range $$p_{thrmin} = 6.6 \text{ kPa} (50 \text{ mmHg}) \leq p_{thr} \leq p_{thrmax} = 13.33 \text{ kPa} (100 \text{ mm Hg}).$$

This has the advantage that the threshold pressure varies within an area being typical for human mean blood pressure values. For the first measuring cycle, a preselected threshold cuff pressure is used, since within said first cycle the mean blood pressure value is not yet known.

According to another aspect of the invention, a further cycle is started after a second time interval $\Delta t_{preii}$ following the first time interval $\Delta t_{pre}$ has ended.

This has the advantage that a very simple method is provided, and simple apparatus to practice the invention is possible. A first counter is provided, and begins incrementing after reaching, at a time $t_1$, the threshold cuff pressure $p_{thr}$ during inflation of the cuff. The first counter starts decrementing after reaching, at a time $t_2$, the threshold pressure $p_{thr}$ again during the cuff pressure reducing step of the said cycle. So, a subsequent next measuring cycle is started when the first counter reach zero.

According to another aspect of the invention, said second cycle is started if both said second time interval $\Delta t_{preII}$ and a minimum dead time interval $\Delta t_{min}$ have ended.

In some cases, if $\Delta t_{pre}$ is a very short interval, it may occur that after end of the second time interval $\Delta t_{preII}$ the cuff pressure has not yet reached $p_{min}$. A deflation of cuff pressure down to $p_{min}$, however, is desirable for convenience of the subject to be measured. For example, it is more agreeable to patient if the cuff is deflated nearly totally, or at least to $p_{min}$, before inflating the cuff again. The minimum dead time interval $\Delta t_{min}$ may be very short and possibly zero, in particular if the second time interval $\Delta t_{preII}$ has ended several seconds before start point time $t_{dz}$ of the dead time interval $\Delta t_{min}$.

According to another aspect of the invention, said second cycle is started if a maximum dead time interval $\Delta t_{max}$ has ended, but said second time interval $\Delta t_{preII}$ has not yet ended.

This has the advantage that in cases of very large second time intervals $\Delta t_{preII}$, and wherein the start time $t_{dz}$ of the dead time interval is in a earlier phase of the said second time interval $\Delta t_{preII}$, the dead time interval is not unnecessarily long. If a second time interval $\Delta t_{preii}$ must be completed, a dead time interval of 10 or 15 seconds may occur. This time is unnecessarily long and results in a reduced number of measuring cycle units per time unit. For example, a maximum dead time interval of 6 seconds is sufficient for human blood pressure measurements. According to the invention, this feature is achieved by connecting the first counter to a second counter incrementing a preselected maximum dead time interval, and said second counter starts incrementing after cuff pressure has reached $p_{min}$. So, a start of the next subsequent cycle can occur if the first counter has reached zero and the second counter has incremented to a minimum dead time interval.

Figure 2:
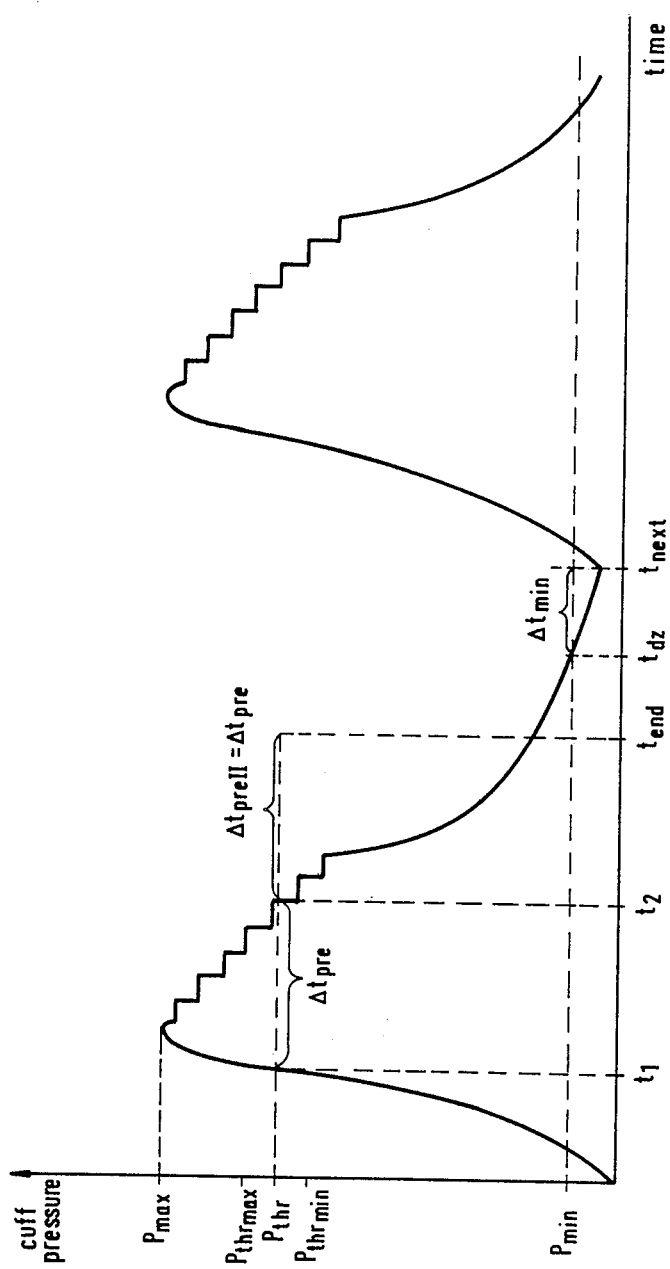
Figure 3:
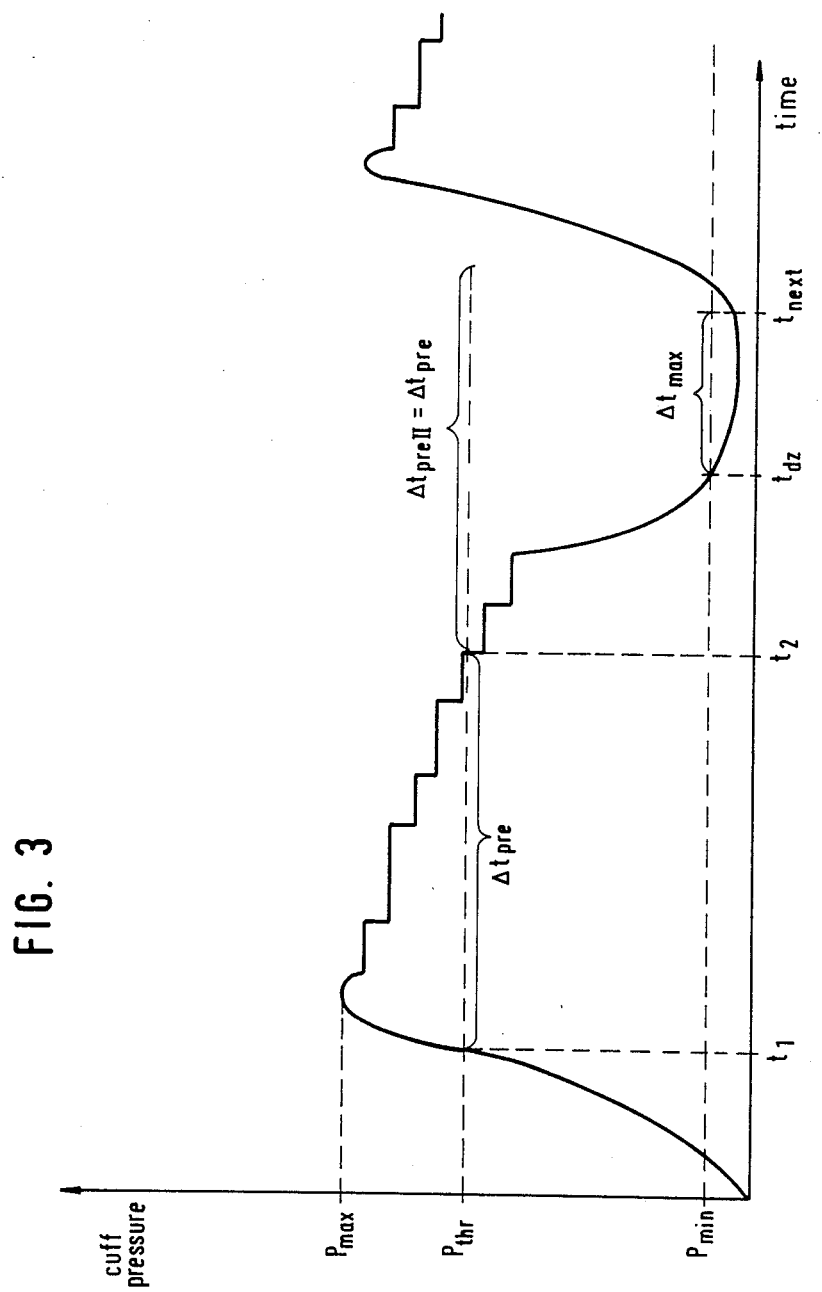
Figure 4:
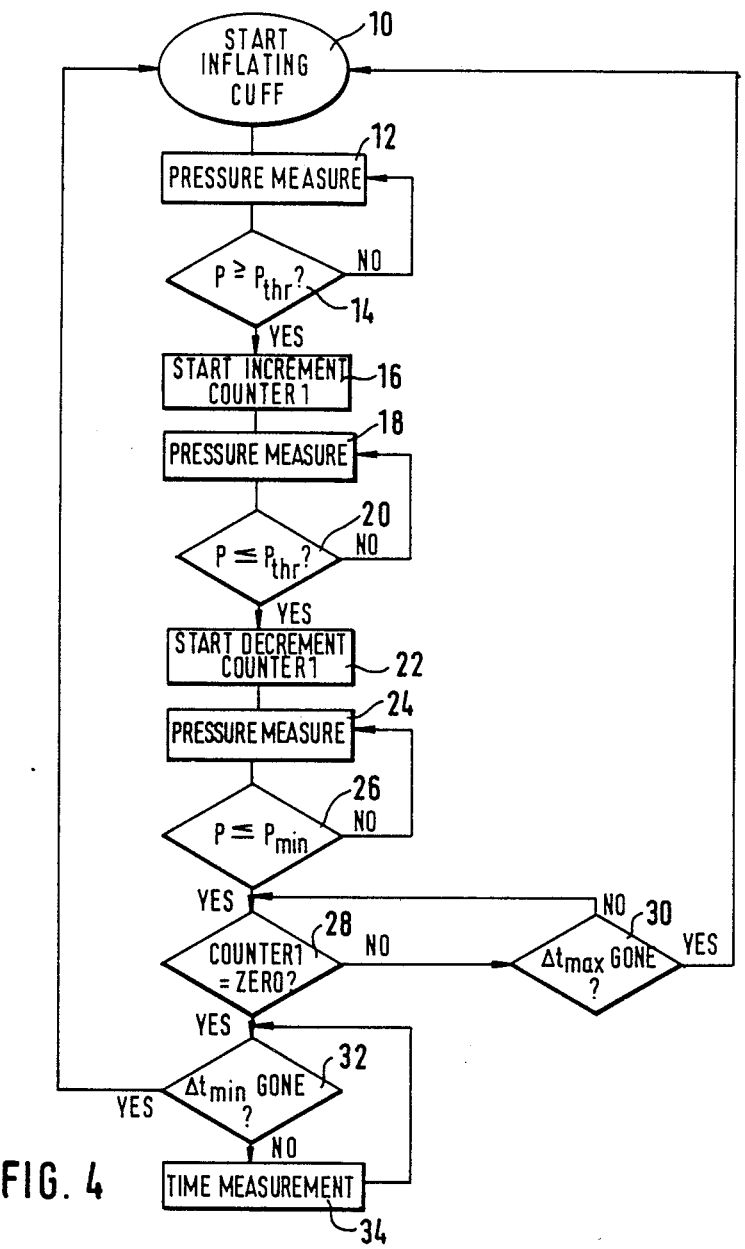

Some embodiments of the present invention will now be described With reference to the accompanying drawings in which FIG. 1 shows a graph having plotted a cuff pressure via time, demonstrating a first embodiment according to the invention, FIG. 2 shows a similar graph as FIG. 1, demonstrating a second embodiment according to the invention, FIG. 3 shows a graph similar to that of FIGS. 1 and 2 demonstrating a third embodiment according to the invention, and FIG. 4 is a flow chart representing the operation of an apparatus according to one embodiment of the invention.

Referring now to FIG. 1, the graph shown is a cuff pressure/time graph of an non-invasive blood pressure measurement. A blood pressure cuff is applied about a subject's artery and inflated above the systolic level $p_{sys}$ up to $p_{max}$, thus fully occluding the artery for a full heart cycle. The cuff pressure is thereafter reduced step by step to permit an increasing flow through the progressively less occluded artery. For example, in accordance with conventional oscillometric techniques, pressure oscillations in the artery are sensed by changes in the counterpressure of the cuff, and in turn by a transducer. A measure of the peak amplitudes of the successively encountered oscillatory complexes (not shown in this graph) are stored in a memory. Also retained is the cuff pressure obtained for each complex peak. As the measurement cycle progresses, the peak amplitude of the blood pressure complexes generally becomes monotonically larger to a maximum and then become monotonically smaller as the cuff pressure continues toward deflation. The peak amplitude of the cuff pressure oscillation complexes and the corresponding occluding cuff pressure values are retained in a computer memory of a processing means.

Inflating of the cuff up to a pressure $p_{max}$ occurs within 2 to 4 seconds, depending on cuff size and arrangement of cuff, e.g. about subject's upper arm or finger.

If cuff pressure is increasing and reaches a threshold cuff pressure value $p_{thr}$ at time $t_1$, a counter or timer is started, incrementing time up to time $t_2$. The time $t_2$ corresponds to the point, the cuff pressure reaches again the threshold value $p_{thr}$ during the stepwise deflating of the cuff.

At time $t_2$, a second time interval of length $\Delta t_{preii} = \Delta t_{pre}$ is started, by decrementing a second counter down to zero.

During the second time interval of length $\Delta t_{preii}$, the cuff is deflated down to a pressure $p_{min}$ at time $t_{dz}$. The pressure $p_{min}$ is in the present embodiment 0.66 kPa (5 mmH). At time $t_{dz}$, a dead time interval $\Delta t_{dea}$ is started, the dead time interval $\Delta t_{dea}$ ends at time $t_{next}$, where time $t_{next}$ is identical with the end of the second time interval $\Delta t_{preii}$. At time $t_{next}$, a next subsequent measuring cycle is initialled by inflating the cuff up to pressure $p_{max}$. Thereafter, a further stepwise deflating of cuff occurs as above described. The cuff works in the stat mode and, therefore uses an array of subsequently following cycles.

The pressure threshold value $p_{thr}$ corresponds to the mean blood pressure $p_{mea}$ of the subject to be measured.

During the first measuring cycle, the mean pressure value is not known, and incrementing of counter starts if cuff pressure reaches minimum threshold pressure value $p_{thrmin}$. Therefore, the start point for the incrementing of first counter at time $t_{1f}$ is somewhat earlier than start time $t_1$. The deviation, however, is very small because of the great gradient of cuff pressure Within the inflating step.

The area of possible threshold pressure values $p_{thr}$ that is the basis for the start of time interval $\Delta t_{pre}$ is limited by maximum and minimum threshold values $p_{thrmax}$ and $p_{thrmin}$, respectively, with $p_{min}=6.6$ kPa (50 mmHg) and $p_{max}=13.33$ kPa (100 mmHg).

As a result, the dead time interval $\Delta t_{dea}$ is a function of the mean pressure value, if $p_{thr}=p_{mea}$, and of the time between two subsequent incremental deflating steps Within one individual measuring cycle.

FIG. 2 shows a graph similar to that of FIG. 1 but illustrates a situation wherein the second time interval $\Delta t_{preii}$ ends before cuff pressure has reached $p_{min}$ during pressure deflation.

This situation may arise if, for example, the mean pressure value is very high and the time interval $\Delta t_{pre}$ very short.

A start of a new cuff inflating step at time $t_{end}$, e.g. after completion of the interval $\Delta t_{preii}$, may result in many measurement cycles per time unit. However, based on the fact that the cuff pressure cannot reach $p_{min}$, the subject to be measured always has the feeling of an inflated compressed cuff around its limb. This compressed situation or feeling is very disagreeable, in particular Within stat mode, nd may result in blood accumulation within the at least partially occluded artery.

Therefore, the cuff pressure is allowed to be reduced at least to $p_{min}$.

Within the FIG. 2 embodiment of the invention, a minimum dead time interval $\Delta t_{min}$ is provided, for example 2 seconds.

It is possible to reduce the dead time interval length $\Delta t_{min}$ to 0, in particular if the cuff pressure between time $t_{end}$ and time $t_{dz}$ is very flat and approximates to $p_{min}$. In these cases, a next measuring cycle can be started immediately after cuff pressure reaches $p_{min}$.

Referring now to FIG. 3, a situation is illustrated wherein the time interval $\Delta t_{pre}$ is so long that said second time interval $\Delta t_{preii}$ ends a long interval after cuff pressure has reached $p_{min}$. If a next subsequent measuring cycle is begun only after the end of the second time interval $\Delta t_{preii}$ an unnecessarily long dead time interval will result.

Therefore, a maximum dead time interval $\Delta t_{max}$, for example 6 seconds, is provided. A next subsequent measuring cycle is started at time $t_{next}$ after maximum dead time interval $\Delta t_{max}$ has been completed, even if second time interval $\Delta t_{preII}$ has not yet ended.

The principles underlying the operation of the apparatus of the present invention are best described with reference to the flow chart in FIG. 4 to which attention should now be directed.

To this end, Proceeding from a start block 10 a step 12 detects the actual cuff pressure. Test 14 determines whether the pressure value is equal to or above a predetermined threshold pressure $p_{thr}$. If $p_{thr}$ is not yet reached, test 12 determines actual cuff pressure again ("NO" branch of test 14). However, if actual cuff pressure has reached $p_{thr}$, block 16 starts incrementing counter 1 ("YES" branch of test 14). Subsequently, step 18 determines the actual cuff pressure. Test 20 determines whether actual cuff pressure has decreased down to $p_{thr}$ again. If threshold pressure $p_{thr}$ has not yet been reached, step 18 further conducts pressure measurements ("NO"branch of test 20). However, if actual pressure p has decreased to threshold pressure $p_{thr}$, block 22 stops incrementing counter 1 and starts decrementing counter 1 ("YES" branch of test 20). Step 24 determines actual cuff pressure and test 26 determines whether actual cuff pressure has reached $p_{min}$. If $p_{min}$ has not reached, step 24 determines actual pressure again ("NO" branch of test 26). However, if $p_{min}$ has been reached, test 28 determines whether counter 1=zero ("YES"0 branch of test 26). If counter 1 has not yet reached zero, test 30 determines whether maximum dead time interval $\Delta t_{max}$ has been completed ("NO" branch of test 28). If the maximum dead time interval has been completed, a new test 30). This situation is illustrated within FIG. 3.

However, if test 30 determines $\Delta t_{max}$ has not been completed, test 28 determines whether counter 1 is zero ("NO" branch of test 30).

However, if test 28 determines counter 1=zero, test 32 determines whether minimum dead time interval $\Delta t_{min}$ has been completed. If the minimum dead time interval has ended, start block 10 initiates a next subsequent cuff inflating step ("YES" branch of test 32). This situation is illustrated within FIG. 1.

However, if test 32 determines $t_{min}$ is not completed, a step 34 conducts time measurements until test 32 indicates that $\Delta t_{min}$ is completed. This situation is illustrated within FIG. 2.

The time measurement of test 32 may occur in connection with a second counter. Said second counter starts incrementing if actual cuff pressure value has decreased to $p_{min}$. Step 34 determines whether second counter has incremented to up to $\neq t_{min}$. Said second counter also can be used for determining whether $\Delta t_{max}$ has ended.

I claim:

1. A method for measuring blood pressure, comprising the steps of:
    applying a blood pressure cuff about a subject's limb containing an artery;
    inflating said cuff to a pressure $p_{max}$ above the systolic pressure $p_{sys}$, thereby occluding said artery;
    reducing cuff pressure from $p_{max}$ to a pressure $p_{min}$ below the diastolic pressure $p_{dia}$, thereby permitting an increasing flow through the progressively less occluded artery;
    detecting effects at the cuff caused by said increasing flow through the progressively less occluded artery;
    processing said detected effects in processing means and displaying the processed effects as the actual blood pressure values; and
    conducting a next subsequent blood pressure measuring cycle after the end of a dead time interval of length $\Delta t_{dea}$, said dead time interval beginning at a time $t_{dz}$ after cuff pressure has reached $p_{min}$;
    characterized by
    starting said next subsequent blood pressure measuring cycle at a time $t_{next}$ that is a function of a cycle specific time interval length $\Delta t_{pre}$ of the preceding measuring cycle.

2. A method according to claim 1, characterized in that the time interval $\Delta t_{pre}$ starts at a time $t_1$ after reaching a threshold cuff pressure $P_{thr}$ during inflating of said cuff, and ends at a time $t_2$ after reaching the said threshold pressure $p_{thr}$ again during the cuff pressure reducing step of said cycle.

3. A method according to claim 2, characterized in that the said threshold pressure $p_{thr}$ corresponds to the mean blood pressure $p_{mea}$.

4. A method according to claim 2, characterized in that the said threshold cuff pressure $p_{thr}$ is limited as $P_{thrmin} \leq p_{thr} \leq p_{thrmax}$.

5. A method according to claim 4, characterized in that for measuring the blood pressure of a human, $p_{thr}$ is $P_{thrmin} = 6.66$ kPa(50 mmHg)$\leq p_{thr} \leq p_{thrmax} = 13.33$ kPa(100 mmHg).

6. A method according to any one of the preceding claims, characterized in that a subsequent second cycle is started if a second time interval of length $\Delta t_{preii} = \Delta t_{pre}$ following the first time interval $t_{pre}$ has ended.

7. A method according to claim 6, characterized in that said second cycle is started if both said second time period $\Delta t_{preii}$ and a predetermined minimum dead time interval of length $\Delta t_{min}$ have ended.

8. A method according to claim 6, characterized in that said second cycle is started if a maximum dead time interval of length $\Delta t_{max}$ has ended, but said second time interval $\Delta t_{preii}$ has not yet ended.

9. An apparatus for automated blood pressure measuring, in particular for cyclic measuring in the stat mode, comprising:
    an inflatable and deflatable pressure cuff, said cuff being applicable about a subject's limb containing an artery;
    means for inflating said cuff to a pressure $p_{max}$ above the systolic pressure $P_{sys}$, thereby occluding said artery;
    means for reducing cuff pressure from $p_{max}$ to a pressure $p_{min}$ below the diastolic pressure $p_{dia}$, thereby permitting an increasing flow through the progressively less occluded artery;
    means for detecting effects at the cuff caused by said increasing flow through the progressively less occluded artery;
    a processing means for processing said detected effects and for displaying the processed effects as the actual blood pressure values, said processing means further comprising means for retarding start of a next measuring cycle until a dead time interval of predetermined length $\Delta t_{dea}$ has ended;
    characterized by
    means for retarding start of the next cycle comprising time incrementing means for storing a cycle specific time interval length $\Delta t_{pre}$ of a preceding measuring cycle, where the retarding means allows start of a next subsequent cycle at a time $t_{next}$ that is a function of said time interval length $\Delta t_{pre}$.

10. Apparatus according to claim 9, characterized in that said retarding means comprises a first counter that starts incrementing after cuff pressure reaches a threshold cuff pressure $p_{thr}$ during inflation of said cuff, and said first counter starts decrementing after cuff pressure reaches the said threshold pressure $p_{thr}$ again during the cuff pressure reducing step of said cycle, and said subsequent next measuring cycle is started if the first counter has decreased to zero.

11. Apparatus according to claim 10, characterized in that said first computer is connected to a second counter, the second counter starts incrementing after cuff pressure has decreased to $p_{min}$, and a start of said next subsequent cycle occurs if said first counter has reached zero and the second counter has incremented to a preselected minimum dead time interval of length $\Delta t_{min}$, or if the second counter has incremented to a preselected maximum dead time interval $\Delta t_{max}$.

* * * * *